(12) United States Patent
Geddes et al.

(10) Patent No.: US 8,182,878 B2
(45) Date of Patent: May 22, 2012

(54) METAL-ENHANCED FLUORESCENCE FROM PLASTIC SUBSTRATES

(75) Inventors: Chris D. Geddes, Bel-Air, MD (US); Kadir Aslan, Baltimore, MD (US)

(73) Assignee: University of Maryland, Baltimore County, Baltimore, MD (US)

( * ) Notice: Subject to any disclaimer, the term of this patent is extended or adjusted under 35 U.S.C. 154(b) by 0 days.

(21) Appl. No.: 13/301,900

(22) Filed: Nov. 22, 2011

(65) Prior Publication Data

US 2012/0063955 A1  Mar. 15, 2012

Related U.S. Application Data

(62) Division of application No. 11/178,560, filed as application No. PCT/US2005/039498 on Oct. 28, 2005, now Pat. No. 8,075,956.

(60) Provisional application No. 60/625,212, filed on Nov. 5, 2004, provisional application No. 60/630,992, filed on Nov. 24, 2004.

(51) Int. Cl.
  *B05D 1/36* (2006.01)
(52) U.S. Cl. ............... 427/402; 427/404; 427/419.1; 427/419.7; 427/419.8; 427/157
(58) Field of Classification Search ............. 427/402, 427/404, 419.1, 419.8, 157
See application file for complete search history.

(56) References Cited

U.S. PATENT DOCUMENTS

| | | | |
|---|---|---|---|
| 4,576,912 A | 3/1986 | Yaverbaum et al. | |
| 5,017,009 A | 5/1991 | Schutt et al. | |
| 5,198,264 A | 3/1993 | Altman et al. | |
| 5,449,918 A | 9/1995 | Krull et al. | |
| 5,618,732 A | 4/1997 | Pease et al. | |
| 5,866,433 A | 2/1999 | Schalkhammer et al. | |
| 5,910,661 A | * 6/1999 | Colvin, Jr. | .......... 250/573 |
| 5,912,313 A | 6/1999 | McIntosh, III et al. | |
| 6,506,314 B1 | 1/2003 | Whitney, Jr. et al. | |
| 7,040,756 B2 | 5/2006 | Qiu et al. | |
| 7,253,452 B2 | 8/2007 | Steckel et al. | |
| 7,348,182 B2 | 3/2008 | Martin et al. | |

(Continued)

FOREIGN PATENT DOCUMENTS

WO    WO89/09408    10/1989

(Continued)

OTHER PUBLICATIONS

Geddes C. D., Cao H., Gryczynski I., Gryczynski Z., Fang J., and Lakowicz J. R. (2003). Metal-enhanced fluorescence due to silver colloids on a planar surface: potential applications of indocyanine green to in vivo imaging. *J. Phys. Chem. A*, 107(28) 3443-3449.

(Continued)

*Primary Examiner* — Eisa Elhilo

(74) *Attorney, Agent, or Firm* — Marianne Fuierer; Moore & Van Allen, PLLC

(57) ABSTRACT

The present invention relates to methods for functionally modifying a polymeric surface for subsequent deposition of metallic particles and/or films, wherein the polymeric surface is modified by increasing hydroxyl and/or amine functional groups thereby providing an activated polymeric surface for deposition of metallic particles to form a fluorescence sensing device. The device can be used for metal-enhanced fluorescence of fluorophores positioned above the metallic particles that can be readily applied to diagnostic or sensing applications of metal-enhanced fluorescence.

13 Claims, 6 Drawing Sheets

U.S. PATENT DOCUMENTS

| | | | |
|---|---|---|---|
| 7,351,590 B2 | 4/2008 | Martin | |
| 7,718,445 B2 | 5/2010 | Martin | |
| 2003/0228682 A1 | 12/2003 | Lakowicz et al. | |
| 2004/0160606 A1 | 8/2004 | Lakowicz et al. | |
| 2005/0053974 A1 | 3/2005 | Lakowicz et al. | |
| 2006/0147927 A1 | 7/2006 | Geddes et al. | |
| 2006/0256331 A1 | 11/2006 | Lakowicz et al. | |
| 2007/0020182 A1 | 1/2007 | Geddes et al. | |
| 2007/0269826 A1 | 11/2007 | Geddes | |
| 2008/0096281 A1 | 4/2008 | Geddes et al. | |
| 2008/0215122 A1 | 9/2008 | Geddes | |

FOREIGN PATENT DOCUMENTS

| | | |
|---|---|---|
| WO | WO 2004/024191 | 3/2004 |

OTHER PUBLICATIONS

Liu Y., Ganser D., Schneider A., Grodzinski P., and Kroutchinina N. (2001). Microfabricated polycarbonate CE Devices for DNA analysis. *Anal. Chem.,* 73(17) 4196-4201.

Martynova L., Locascio L. E., Gaitan M., Kramer G. W., Christensen R. G. And MacCrehan W. (1997). Fabrication of plastic microfluid channels by imprinting methods. *Anal. Chem.,* 69(23) 4783-4789.

Dauginet L., Duwez A. S., Legras R. and Demoustier-Champagne S. (2001). Surface modification of polycarbonate and poly(ethylene terephthalate) films and membranes by polyelectrolyte deposition. *Langmuir,* 17(13) 3952-3957.

Rivas L., Sanchez-Cortes S., Garcia-Ramos J. V. and Morcillo G. (2001). Growth of silver colloidal particles obtained by citrate reduction to increase the Ramen enhancement factor. *Langmuir,* 17(3) 574-577.

Ward W. and McCarthy T. J. (1989) In Encyclopedia of Polymer Science and Engineering, $2^{nd}$ ed.; Mark, H. F., Bikales, N. M., Overberger, C. G., Menges, G., Kroschwitz, J. I., Eds.; John Wiley and Sons: New York, 1989; suppl. vol. pp. 674-689.

Coates D. M. and Kaplan S. L. (1996) Modification of Polymeric Material Surfaces with Plasmas, Chapter IV of Plasma Processing of Advanced Materials, edited by George A. Collins and Donald J. Rej, MRS Bulletin.

Lakowicz J. R., Gryczynski I., Shen Y. B., Malicka J., and Gryczynski Z., (2001). Intensified fluorescence. *Photonics Spectra,* 35(10) 96-104.

Geddes C. D. and Lakowicz J. R. (2002). Metal-enhanced fluorescence. *J. Fluorescence,* 12(2) 121-129.

Lakowicz J. R. (2001). Radiative decay engineering: Biophysical and biomedical applications. *Anal. Biochem.,* 298(1)1-24.

Lakowicz J. R., Shen Y., D'Auria S., Malicka J., Fang J., Grcyzynski Z. and Gryczynski I. (2002). Radiative decay engineering 2. Effects of silver island films on fluorescence intensity, lifetimes, and resonance energy transfer. *Anal. Biochem.,* 301(2) 261-277.

Geddes C. D., Aslan K., Gryczynski I., Malicka J., and Lakowicz J. R. (2004). Noble metal nanostructure for metal-enhanced fluorescence, Reviews in Fluorescence 2004, Ed. C. D. Geddes, pp. 365401, Springer, New York.

Liu Y., Ganser D., Schneider A., Grodzinski P. And Kroutchinina N. (2001). Microfabricated polycarbonate CE Devices for DNA analysis. *Anal. Chem.,* 73(17) 4196-4201.

Roberts M. A., Rossier J. S., Bercier P., and Girault H. (1997). UV laser machined polymer substrates for the development of microdiagnostic systems. *Anal. Chem.,* 69(11) 2035-2042.

Xu J., Locascio L., Gaitan M. and Lee C. S. (2000). Room-temperature imprinting method for plastic microchannel fabrication. *Anal. Chem.,* 72(8) 1930-1933.

McCormick R. M., Nelson R. J., Alonso-Amigo M. G., Benvegnu D. J. And Hooper H. H. (1997). Microchannel electrophoretic separations of DNA in injection-molded plastic substrates. *Anal. Chem.,* 69(14) 2626-2630.

Xu Y., Vaidya B., Patel A. B., Ford S. M., McCarley R. L. and Soper S. A. (2003). Solid-phase reversible immobilization in microfluidic chips for the purification of dye-labeled DNA sequencing fragments. *Anal. Chem.,* 75(13) 2975-2984.

Wokaun A., Lutz H. P., King A. P., Wild U. P. and Ernst R. R (1983). Energy transfer in surface enhanced fluorescence. *J. Chem. Phys.,* 79(1), 509-514.

Holland W. R. and Hall D. G. (1985). Waveguide mode enhancement of molecular fluorescence. *Optics Letts.,* 10(8) 414-416.

Glass A. M., Liao P. F., Bergman J. G. and Olson D. H. (1980). Interaction of metal particles with adsorbed dye molecules: absorption and luminescence. *Optics Letts.,* 5(9), 368-370.

Barnes W. L. (1998). Fluorescence near interfaces: The role of photonic mode density, *J. Modern Optics,* 45(4) 661-699.

Gryczynski I., Malicka J., Gryczynski L., Geddes C. D. and Lakowicz J. R. (2002) The CFS engineers the intrinsic radiative decay rate of low quantum yield fluorophores, *J. Fluorescence,* 12(1), 11-13.

Shirtcliffe N., Nickel U. and Schneider S. (1999). Reproducible preparation of silver sols with small particle size using borohydride reduction: For use as nuclei for preparation of large particles. *J. Colloid Interface Sci.,* 211(1) 122-129.

Pastoriza-Santos I. and Liz-Marzan L. M. (2000). Reduction of silver nanoparticles in DMF. Formation of monolayers and stable colloids. *Pure Appl. Chem.,* 72(1-2) 8390.

Pastoriza-Santos I., Serra-Rodriquez C. and Liz-Marzan L. M. (2000). Self-assembly of silver particle monolayers on glass from $Ag^+$ solutions in DMF. *J. Colloid Interface Sci.,* 221(2) 236-241.

Bright R., Musick M. D. and Natan M. J. (1998). Preparation and characterization of Ag colloid monolayers. *Langmuir,* 14(20) 5695-5701.

Ni F. and Cotton T. M. (1986). Chemical procedure for preparing surface-enhanced Raman scattering active silver films. *Anal. Chem.,* 58(14) 3159-5163.

M. Borner, M. Kohl, F. Pantenburg, W. Bather, H. Hein, W. Schomburg. (1996). Microsyst Technol, 2, 149-152.

\* cited by examiner

METAL-ENHANCED FLUORESCENCE FROM PLASTIC SUBSTRATES

CROSS-REFERENCE TO RELATED APPLICATIONS

This application is a divisional application of co-pending U.S. patent application Ser. No. 11/718,560, filed on Apr. 8, 2008, now U.S. Pat. No. 8,075,956, which is turn claims priority of International Patent Application No. PCT/US2005/039498 is filed on Oct. 28, 2005, which in turn claims priority of U.S. Provisional Application No. 60/625,212 filed on Nov. 5, 2004 and U.S. Provisional Patent Application No. 60/630,992 filed on Nov. 24, 2004.

GOVERNMENT INTEREST

The invention disclosed herein was made with U.S. Government support under Grant No. GM070929-01 from the NIH. Accordingly, the U.S. Government has certain rights in this invention

BACKGROUND OF THE INVENTION

1. Technical Field

The present invention relate generally to a fluorescence sensing system, and more particularly, to a system including a polymeric surface having metallic particles deposited thereon and method of forming such metallizable polymeric surfaces.

2. Description of Related Art

Fluorescence systems have become a dominant technology in medical testing, drug discovery, biotechnology and cellular imaging. The use of fluorescence technology has greatly enhanced the ability to detect specific molecules leading to rapid advancements in diagnostics. For example, fluorescence detection is widely used in medical testing and DNA analysis because of the high degree of sensitivity obtained using fluorescent techniques. Importantly a small numbers of molecules can be detected using fluorescence technology. Typically, extrinsic fluorophores are added covalently or non-covalently to allow molecules that do not ordinarily fluoresce or do not fluoresce at useful levels to be detected.

Detection of the molecule of interest is generally limited by the properties of the fluorophore used. In some cases, labeling a biomolecule with an extrinsic fluorophore can alter the biological activity of the biomolecule potentially creating experimental artifacts. Problems with current fluorescent techniques stem in part from the low fluorescent intensities of commonly used fluorophores. Additionally, background fluorescence can be significant when using low wavelength excitation radiation required by some fluorophores or when large quantities of fluorophores are required.

At present, the use of noble metals, particles, and surfaces for applications in sensing, is biotechnology, and nanotechnology has drawn considerable attention. For example, U.S. application Ser. No. 10/073,625, discloses compositions and methods for increasing fluorescence intensity of molecules by adding either intrinsic or extrinsic fluorophores, and positioning same at a specific distance from a metal particle. Specifically, metal particles, deposited on glass or quartz type material, and biomolecules with a fluorophore are positioned at a distance from the metal particles. This positioning of the fluorophore at a specific distance from the metal particle can alter or increase the intrinsic emission of electromagnetic radiation from the biomolecule in response to an amount of exciting electromagnetic radiation.

Favorable effects of silver particles on fluorophores include increased quantum yields, decreased lifetimes, and increased photostability of fluorophores commonly used in biological research. These effects of conducting metallic particles on fluorescence have been the subject of numerous theoretical studies related to surface-enhanced Raman scattering and the application of these considerations to molecular fluorescence. There is now interest in using the remarkable properties of metallic islands, colloids or continuous surfaces.

Consequently, it is of interest to develop convenient methods for forming metallic particles and/or films on different surfaces. These approaches include electroless deposition, electroplating on insulators, lithography, and the formation of colloids under constant reagent flow. Metallic particles can be assembled into films using electrophoresis, and gold particles have been used for the on-demand electrochemical release of DNA. It is anticipated that many of these approaches will find uses in medical diagnostics and lab-on-a-chip-type applications.

Heretofore, all of these findings have been based on metallic silver being deposited on glass or quartz type substrates with a subsequent spacer layer used to separate the fluorophore from the metal. Thus, it would be of great value to devise methods for localized or continuous silver deposition on other surfaces that are more flexible that glass planar surfaces or glass-based substrates.

SUMMARY OF INVENTION

The present invention relates to methods for functionally modifying a polymeric surface for subsequent deposition of metallic particles and/or films, wherein a polymeric surface comprising low density of functional groups is modified by increasing the number of hydroxyl and/or amine functional groups relative to an unmodified surface thereby providing an activated polymeric surface useful for metal-enhanced fluorescence of fluorophores positioned above the metallic particles that can be readily applied to diagnostic or sensing devices for applications of metal-enhanced fluorescence (MEF).

In another aspect, the present invention relates to uses of such polymeric surfaces for enhancement of effect of fluorophores near metallic surfaces comprising at least silver particles. These effects include increased quantum yields, decreased lifetimes, increased photostability, and increased energy transfer. These effects are due to interactions of the excited-state fluorophores with the surface plasmon resonances on the metallic surfaces. These interactions of the fluorophore with the metal surface can result in increased rates of excitation, quenching, increased intensities, and/or increased quantum yield.

In yet another aspect, the present invention relates to a method for depositing a noble metal on a polymeric surface, the method comprising:

a) providing a polymeric material with low density of hydroxyl surface functionality;

b) modifying the polymeric material with a chemical or physical etching agent, wherein the modified polymeric material comprises an increased number of exposed hydroxyl groups or amine group on the polymeric surface relative to an unmodified surface;

c) silylating the modified polymeric material to provide an amino-terminated polymeric material; and d) depositing a noble metal on the amino-terminated polymeric material.

Subsequent to the deposition of the noble metal particles, a spacer can be applied to the metal surface to provide a required distance from the metal surface to the fluorophore for metal enhanced fluorescence.

In yet another aspect, the present invention relates to a method for forming a patterned metallic surface on a polymeric substrate, the method comprising:

(a) providing a polymeric substrate;
(b) etching the surface of the polymeric substrate with an etching agent to increase hydroxyl groups on the surface of polymer substrate relative to a non-etched polymeric surface
(c) contacting the polymeric substrate having increased hydroxyl groups with a silylating agent to replace at least some of the hydroxyl groups with amine groups to form an amino-activated surface; and
(d) depositing noble metal particles on the amine activated polymeric substrate.

A still further aspect of the present invention relates to a fluorescence sensing device comprising:

a modified polymeric surface comprising amino-terminated functional groups;
nanometer sized metallic particles deposited on the modified polymeric surface, wherein the metallic particles can be any geometric shape; and
a fluorophore compound communicatively linked to the metal particles at a sufficient distance to enhance the fluorescence of the fluorophore when exposed to electromagnetic radiation from an electromagnetic source.

The present invention further comprises a detection device for detecting fluorescence emissions including, but not limited to visual inspection, digital (CCD) cameras, video cameras, photographic film, or the use of current instrumentation such as laser scanning devices, fluorometers, luminometers, photodiodes, quantum counters, plate readers, epifluorescence microscopes, scanning microscopes, confocal microscopes, capillary electrophoresis detectors, or other light detectors capable of detecting the presence, location, intensity, excitation and emission spectra, fluorescence polarization, fluorescence lifetime, and other physical properties of the fluorescent signal.

A source of electromagnetic energy may include lasers emitting radiation from the UV to IR spectrum, masers, LEDs, incandescent lamps, etc, and which will be determined by the frequency or wavelength of energy required for excitation of the specific fluorophore.

A further aspect of the present invention, relates to a kit for detecting a target molecule in a sample, the kit comprising a container comprising a layer of immobilized metal particles deposited on a polymeric substrate, wherein an immobilized probe is connected to the metal particles and wherein the immobilized probe has an affinity for the target molecule; and a fluorophore having an affinity for the target molecule, wherein the binding of the target molecule to both the immobilized probe and fluorophore causes the fluorophore to be positioned a sufficient distance from the immobilized metal particles to enhance fluorescence emission, Other aspects and advantages of the invention will be more fully apparent from the ensuing disclosure and appended claims.

DETAILED DESCRIPTION OF THE INVENTION

Figure 1:
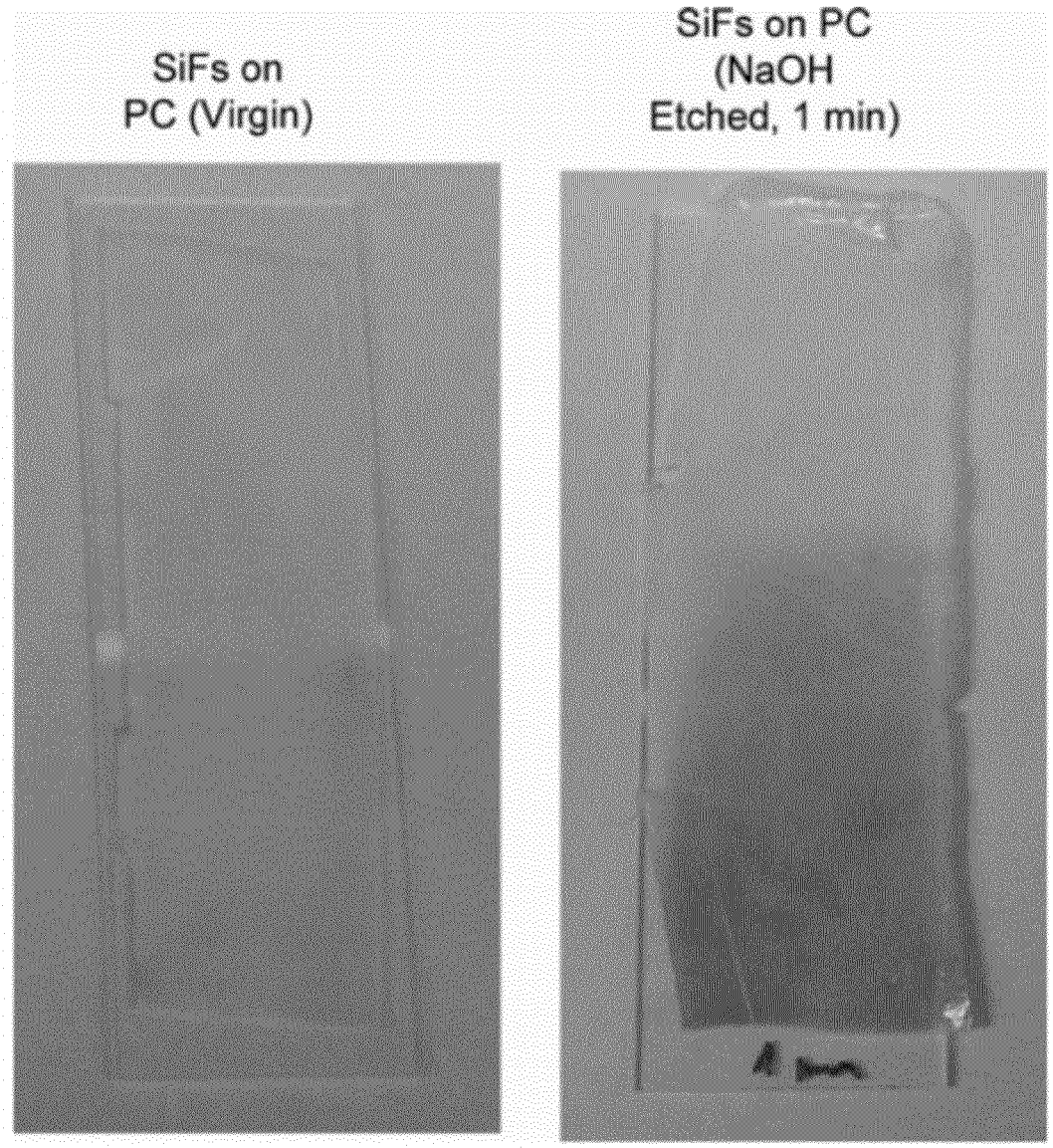
FIG. 1 shows photographs of two (2) plastic films mounted on glass slides. Left—silver island films (SiFs) deposited on unmodified PC and Right—SiFs deposited on NaOH etched PC.

In the past several years a number of different metal-fluorophore combinations and geometries [1-5] have been developed, which ultimately yielded significantly brighter and more photostable fluorophores. These advances were not due to chemical structure modifications, but are due to the control of the intrinsic fluorophore radiative decay rate. Specifically, this new technology has been named this metal-enhanced fluorescence [1,5] and radiative decay Engineering (RDE) [2,3]. Primarily with the use of MEF, silver nanostructures deposited onto clean glass microscope slides or quartz plates have been used. This has been because the chemistries of the surface of glass are well established and therefore the covalent immobilization of silver nanostructures onto glass less arduous and indeed reproducibly reliable.

Polymer substrates are known to be very promising substrates for a variety of applications and industrial interest in utilizing plastics is primarily driven by the fact that these materials are less expensive and easier in mass production than silica based substrates [6]. There are also a wide variety of materials to choose from with an even greater array of chemical and physical properties [6].

The present invention shows that polymeric substrates can be used as substrates for metal-enhanced fluorescence, which, given their cost, are likely to be much better received by industry. While high surface density of either hydroxyl or amino groups, which are readily used for silver deposition, the present invention provides modification of a polymeric surface exhibiting low density of surface functionality. This modification allows for MEF to be introduced into already existing plastic based technologies, such as with plastic high-throughput screening well plates and fluorescence based clinical assays. The practical approaches to polymer surface modification are corona discharge treatment, plasma, surface graft, light and chemical modification [12].

The presence of a nearby metal film, island or particle can also alter the emission properties of fluorophores. The most well known effect is the quenching of fluorescence by a near-by metal. The emission of fluorophores within 50 Å of a metal surface is almost completely quenched. This effect is used in fluorescence microscopy with evanescent wave excitation. For a fluorophore located on a cell membrane and near the quartz-water interface the fluorescence emission is quenched, allowing selective observation of the emission from a fluorophore in the cytoplasmic region of the cell, which is more distant from the solid-liquid interface. In addition to quenching, metal surfaces or particles can cause significant increases in fluorescence. Remarkably, depending on the distance and geometry, metal surfaces or particles can result in enhancement factors of up to 1000 for the fluorescence emission [17-19]. Fluorophores near a metal film are not expected to emit isotropically, but rather the emission is directed into selected directions that are dependent on the sample configuration and the nature of the metallic surface. In addition to directionality, the decay times of fluorophores are altered by the metal. In fact, the lifetimes of fluorophores placed at fixed distances from a continuous metallic-surface oscillate with distance [20].

The effects of metallic particles and surfaces on fluorophores are due to at least three known mechanisms. One mechanism is energy transfer quenching, $k_m$, to the metals with a $d^{-3}$ dependence. This quenching can be understood by damping of the dipole oscillations by the nearby metal. A second mechanism is an increase in the emission intensity due to the metal increasing the local incident field on the fluorophore, $E_m$, with a maximum theoretical enhancement effect of about 140. This effect has been observed for metal colloids and is appropriately called the "Lightning Rod effect." This enhancement can be understood as due to the metal particles on concentrating the local field and subsequently increasing the rate of excitation. The third mechanism is that a nearby metal can increase the intrinsic decay rate of the fluorophore, $\Gamma_m$, that is, to modify the rate at which the fluorophore emits photons. These later two fluorophore-metal interactions offer remarkable opportunities for advanced fluorescence assay-technology.

The distance dependence of fluorescence enhancements and those of quenching may be determined by standard methods disclosed herein.

In fluorescence, the spectral observables are governed by the magnitude of $\Gamma$, the radiative rate, relative to the sum of the non-radiative decay rates, $k_{nr}$ such as internal conversion and quenching. In the absence of metallic particles or surfaces, the quantum yield, $Q_0$ and fluorescence lifetime $\tau_0$ are given by:

$$Q_0 = \frac{\Gamma}{\Gamma + k_{nr}}$$

$$\tau_0 = \frac{1}{\Gamma + k_{nr}}$$

Fluorophores with high radiative rates have high quantum yields and short lifetimes Increasing the quantum yield requires decreasing the non-radiative rates $k_{nr}$, which is often only accomplished when using low solution temperatures or a fluorophore binding in a more rigid environment. The natural lifetime of a fluorophore, $\tau_N$, is the inverse of the radiative decay rate or the lifetime, which would be observed if the quantum yield were unity. This value is determined by the oscillator strength (extinction coefficient) of the electronic transition [21-24]. The extinction coefficients of chromophores are only very slightly dependent on their environment. Hence, for almost all examples currently employed in fluorescence spectroscopy, the radiative decay rate is essentially constant.

Figure 3:
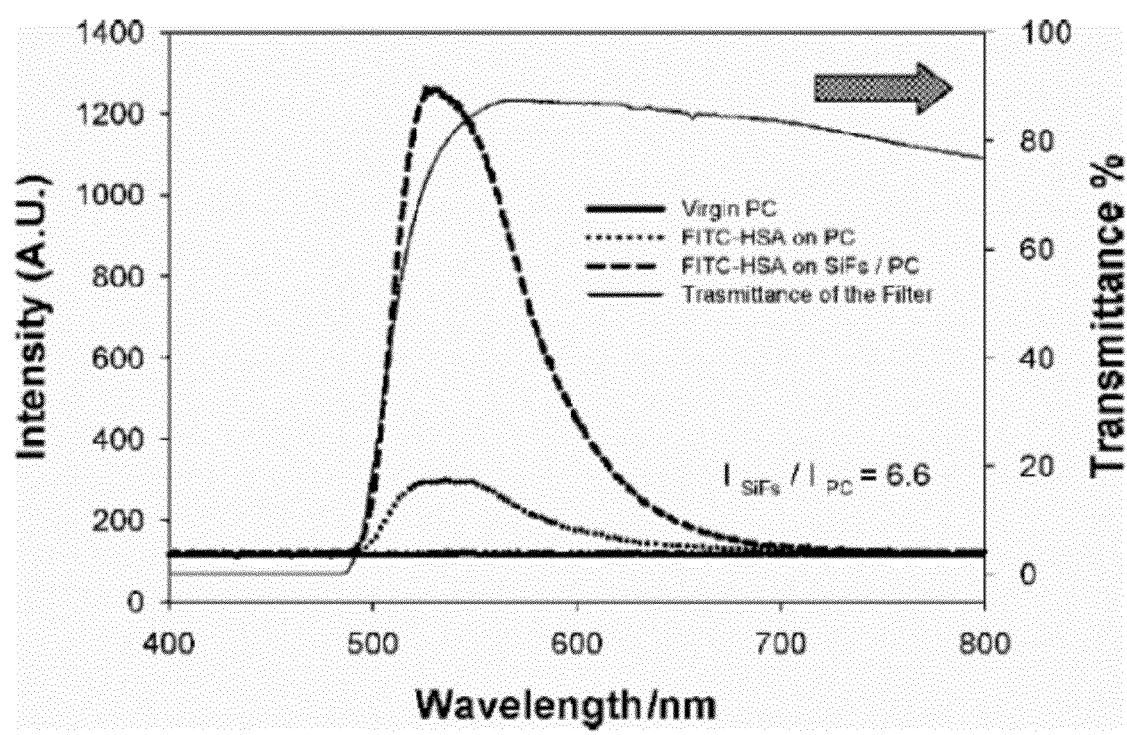
FIG. 3 shows emission spectra of FITC-HSA monolayers on modified PC with and without SiFs and on virgin PC (unmodified). The transmission spectra of the 500 nm is cut-off filter is also shown.

The concept of modifying the radiative decay rate of fluorophores is unfamiliar to most spectroscopists. It is therefore intuitive to consider the novel effects of fluorescence enhancement due to metal particles, m, by assuming an additional radiative rate, $\Gamma_m$, as shown in FIG. 3. In this case, the quantum yield and lifetime are given by:

$$Q_m = \frac{\Gamma + \Gamma_m}{\Gamma + \Gamma_m + k_{nr}}$$

$$\tau_m = \frac{1}{\Gamma + \Gamma_m + k_{nr}}$$

Figure 4:
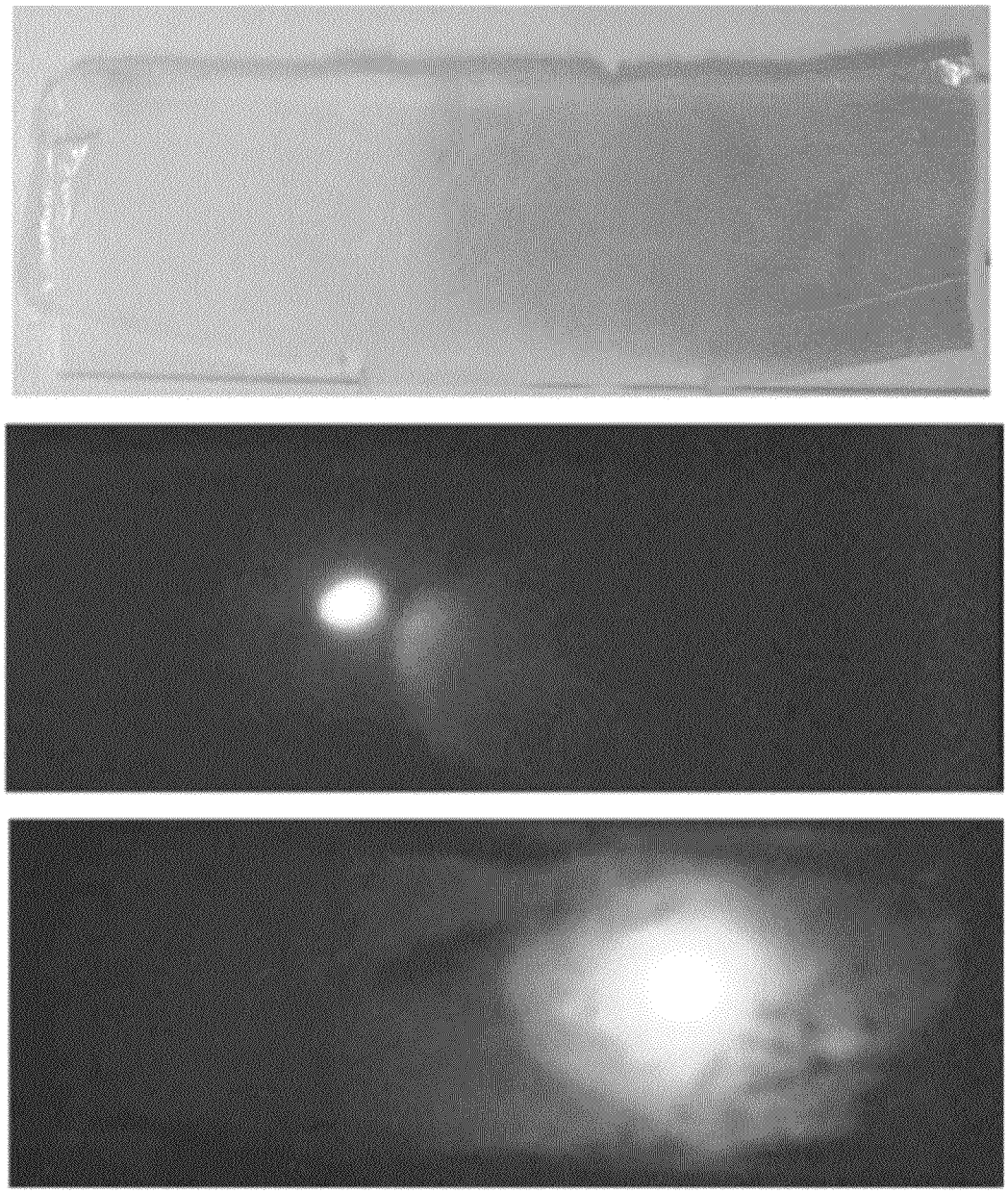
FIG. 4 shows photographs: SiF coated modified plastic, Top; the emission of fluorescein labeled human serum albumin (FITC-HAS) on the unsilvered modified PC, Middle; and on the silvered and modified PC, Bottom.

These equations result in important predictions for a fluorophore near a metal surface. As $\Gamma_m$ increases, the fluorescence quantum yield increases while the lifetime decreases, as shown in FIG. 4, which is converse to the free space condition where both change in unison. An ability to modify and control the radiative decay rate ($\Gamma+\Gamma_m$) can have profound implications for the use of fluorescence in basic research and its applications.

The reduction in lifetime of a fluorophore near a metal is due to an interaction between fluorophore and metal particle, which enhances the radiative decay rate (quantum yield increase) or depending on distance, $d^{-3}$, causes quenching. A shorter excited-state lifetime also allows for less photochemical reactions which subsequently results in increased fluorophore photostability.

Fluorophore photostability is a primary concern in many applications of fluorescence. This is particularly true in recent trends in single molecule spectroscopy. A shorter lifetime also allows for a larger photon flux. The maximum number of photons that are emitted by a fluorophore each second is roughly limited by the lifetime of its excited state. For example, a 10 ns lifetime can yield about $10^8$ photons per second per molecule, but in practice, only $10^3$ photons can readily be observed. The small number of observed photons is typically due to both photodestruction and isotropic emission. If the metal surface decreases the lifetime then one can obtain more photons per second per molecule by appropriately increasing the incident intensity. On the other hand, the metal enhanced fluorescence effects of the present invention enhances intensity while simultaneously shortening the lifetime. Decreases in the excitation intensity will still result in increases in the emission intensity and therefore photostability.

The ability to increase the radiative decay rate suggests that any chromophore, even non-fluorescent species such as bilirubin, fullerenes, metal-ligand complexes or porphyrins could display usefully high quantum yields when appropriately placed near a metal surface.

The effects of metal surface-fluorophore interactions are highly dependent upon distance and the nature of the metal surface. The emission enhancement is observed when fluorophore distances near 4-50 nm to the metal surfaces. At this scale, there are few phenomena that provide opportunities for extremely high levels of assay—sensing, manipulation, and control. In addition, devices at this scale may lead to dramatically enhanced performance, sensitivity, and reliability with dramatically decreased size, weight, and therefore cost, important considerations for field-deployable bio-terrorism anthrax sensors. Slightly different effects can be expected for mirrors, sub-wavelength or semi-transparent metal surfaces, silver island films or metal colloids.

Before the present invention is disclosed and described, it is to be understood that this invention is not limited to the particular process steps and materials disclosed herein as such process steps and materials may vary somewhat. It is also to be understood that the terminology used herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural references unless the content clearly dictates otherwise.

The term "fluorophore" means any substance that emits electromagnetic energy such as light at a certain wavelength (emission wavelength) when the substance is illuminated by radiation of a different wavelength (excitation wavelength). Extrinsic fluorophores refer to fluorophores bound to another substance. Intrinsic fluorophores refer to substances that are fluorophores themselves. Exemplary fluorophores include but are not limited to those listed in the Molecular Probes Catalogue, which is incorporated by reference herein. Representative fluorophores include but are not limited to Alexa Fluor® 350, Dansyl Chloride (DNS-Cl), 5-(iodoacetamida) fluoroscein (5-IAF); fluoroscein 5-isothiocyanate (FITC), tetramethylrhodamine 5-(and 6-)isothiocyanate (TRITC), 6-acryloyl-2-dimethylaminonaphthalene (acrylodan), 7-nitrobenzo-2-oxa-1,3-diazol-4-yl chloride (NBD-Cl), ethidium bromide, Lucifer Yellow, 5-carboxyrhodamine 6G hydrochloride, Lissamine rhodamine B sulfonyl chloride, Texas Red™, sulfonyl chloride, naphthalamine sulfonic acids including but not limited to 1-anilinonaphthalene-8-sulfonic acid (ANS) and 6-(p-toluidinyl)naphthalene-2-sulfonic acid (TNS), Anthroyl fatty acid, DPH, Parinaric acid, TMA-DPH, Fluorenyl fatty acid, Fluorescein-phosphatidylethanolamine, Texas red-phosphatidylethanolamine, Pyrenyl-phophatidylcholine, Fluorenyl-phosphotidylcholine, Merocyanine 540, 1-(3-sulfonatopropyl)-4-[-.beta.-[2[(di-n-butylamino)-6naphthyl]vinyl]pyridinium betaine (Naphtyl Styryl), 3,3'dipropylthiadicarbocyanine (diS—$C_3$-(5)), 4-(p-dipentylaminostyryl)-1-methylpyridinium (di-5-ASP), Cy-3 Iodo Acetamide, Cy-5-N-Hydroxysuccinimide, Cy-7-Isothiocyanate, rhodamine 800, IR-125, Thiazole Orange, Azure B, Nile Blue, Al Phthalocyanine, Oxaxine 1,4',6-diamidino-2-phenylindole (DAPI), Hoechst 33342, TOTO, Acridine Orange, Ethidium Homodimer, N(ethoxycarbonylmethyl)-6-methoxyquinolinium (MQAE), Fura-2, Calcium Green, Carboxy SNARF-6, BAPTA, coumarin, phytofluors, Coronene, and metal-ligand complexes.

Representative intrinsic fluorophores include but are not limited to organic compounds having aromatic ring structures including but not limited to NADH, FAD, tyrosine, tryptophan, purines, pyrirmidines, lipids, fatty acids, nucleic acids, nucleotides, nucleosides, amino acids, proteins, peptides, DNA, RNA, sugars, and vitamins. Additional suitable fluorophores include enzyme-cofactors; lanthanide, green fluorescent protein, yellow fluorescent protein, red fluorescent protein, or mutants and derivates thereof.

In accordance with this invention, any flexible or rigid polymeric substrate can be utilized in the process of this invention. Typical film or relatively rigid substrates include polymeric compositions containing polyamide, polycarbonate, polyester, polyetherimide, polyimide, polynitrocellulose, polyolefins such as polyethylene, polypropylene, poly(ethylenevinylacetate), poly-2-pentene, EPDM, polyionomers such as Surlyn®, polyphenylene oxide, polyphenylene sulfide, polysulfone, polystyrene, polyvinyl-vinylidine chloride or fluoride or the like.

Alternatively, rigid substrates may include any rigid substrates coated with a polymeric surface including, but not limited to, ceramics, glass, paper compositions or the like; or composite substrates such as epoxy-fiber glass, epoxy-paper laminate, paper-fiber glass laminate, urea formaldehyde-fiber glass laminate, phenolic-fiber glass laminate, a polymeric fluorocarbon-fiber glass laminate, or the like or with other reinforcing components such as carbon fiber, synthetic polymer fiber, pigments or the like.

The preferred substrates include polycarbonates, polyesters, polyetherimides, polyimide, polyolefins or polysulfone. More preferably, the substrate is a polymeric material that upon treatment with an activation agent increases hydroxyl groups on the surface of the polymeric substrate. Most preferably, the polymeric substrate includes polyimides (Kapton®); polyesters (Mylar®); polycarbonates (Lexan®) and polyetherimides (Ultem®) due to their physical and thermal stability over wide temperature ranges, chemical inertness and radiation resistance.

It may be necessary to pre-treat the polymeric substrate in order to remove any unwanted surface contamination before the functionalization process. For example, the surface of polyethylene is typically contaminated with low molecular-weight, wax-like, incompletely polymerized oligomers of ethylene, the monomer for polyethylene. These poorly adherent fragments should be removed and can be easily and quickly degraded into volatile compounds and can be removed by short plasma treatment thereby leaving the polymeric surface essentially intact and minimally etched if short treatment times are used. For example, argon may be used since the plasma treatment to remove contaminants and it time is relatively short thereby is reducing any unwanted chemistry.

A typical cleaning procedure for example polyethylene would be to treat with Argon at a pressure of 0.01 to 0.4 Torr, with a power density of about 0.5 W/cm$^2$ at 13.56 MHz rf on parallel-plate electrodes. Once contaminants are removed, if necessary, a more stable polymer surface is exposed to an activating agent to provide an increased density of hydroxyl or amine functional groups of the surface of the polymeric substrate, relative to a polymeric surface without the activation treatment. [16].

After cleaning or removal of contaminants, if necessary, of the surface of the polymeric substrate, etching is used to increase the density of functional groups on the surface substrate. The polymeric substrate is etched to provide attraction sites for subsequent catalytic metal deposition.

Etching involves solvating the polymeric substrate with a solvent to chemically modifying the surface substrate to provide attraction sites for catalytic metal deposition. For the present invention, a wide variety of etchants are satisfactory as long as selective solvation and chemical modification occurs. Typically, the first step in this process is to create hydroxyl groups (if they do not already exist on the support) or amino groups on the support. Surface activation comprises formation of reactive hydrogen groups in a surface region of the substrate, wherein the reactive hydrogen groups are selected from one or more members of the group comprising OH, OOH and COOH groups.

Some polymeric surfaces may be activated by a wet process, comprising hydrolysis by a dilute aqueous base, such as NaOH, NH$_4$OH, LiOH, KOH or N(CH$_3$)$_4$OH. Preferably, the base hydrolysis of the polymeric surface is performed in aqueous NaOH at a temperature ranging from about 15° C. to about 45° C. for a time ranging from about 10 minutes to about 5 hours, and more preferably from about 1 minute to one hour depending on the polymeric material.

In another embodiment, the surface activation step of the present invention may comprise formation of reactive hydrogen groups in a surface region of the polymeric surface by photo-oxidation, which preferably comprises irradiation of the surface of the substrate with a dose of UV radiation, in the presence of oxygen.

UV radiation comprises radiation in the region of the electromagnetic spectrum including wavelengths from about 100 to about 380 nm. The preferred wavelengths to which substrates are exposed in the activation step is variable, and depends on the composition of the specific substrate. For example, polyimides or polycarbonates are preferably irradiated with UV radiation having wavelengths from about 200 to about 300 nm.

Preferably, the source of UV radiation is a low-pressure quartz-mercury lamp having an intensity of from about 1 to about 5 mW/cm$^2$. The duration of the UV exposure is preferably from about 1 minute to about 120 minutes, more preferably from about 2 to about 20 minutes. The preferred UV dose is from about 0.7 J/cm$^2$ to about 5 J/cm$^2$, more preferably from about 2 to about 5 J/cm$^2$, depending on the substrate and the amount of functionalization desired. These parameters are preferred for production of reactive hydrogen groups. Irradiation for longer times and/or at higher intensities can result in a decrease in the amount of active hydrogen groups and an increase in the amount of other oxygen-containing groups such as (ketone) carbonyl groups.

The activation of the polymeric surface substrate in the presence of UV radiation is believed to be a result of simultaneous excitement of molecules comprising the substrate and attack by molecular oxygen, as well as ozone, atomic oxygen and singlet oxygen generated from molecular oxygen by UV radiation.

As a result of the photochemically-induced oxidative surface modification, oxygen-containing reactive hydrogen groups such as OH, OOH and COOH are formed on the surface of the substrate. Preferably, surface activation of the substrate occurs to a depth of about 200 to about 1000 nm below the surface of the substrate, producing a surface region of the substrate containing active hydrogen groups.

It is possible to monitor the progress of the surface activation reaction by measuring the water contact angle of the substrate surface at different times during the is activation step because the water contact angle decreases due to the increased hydrophilicity of the polymer surfaces.

Although the surface activation substrates has been described above with reference to oxidative activation by molecular oxygen and UV and a wet process for polyimides, it is to be understood that other processes may be used to activate the polymeric surface of a substrate. For example, dry processes such as oxidation in oxygen containing plasmas, oxygen ion-beam modification, oxidation by fast atomic oxygen (FAO), and corona discharge may be used to produce reactive hydrogen groups on the surface of a solid substrate.

Next the activated polymeric surface having an increased number of hydroxyl groups is silylated by reacting at least some of the reactive hydrogen groups, formed in the upper region of the substrate by the surface activation step, with a silylating agent, whereby silicon-containing groups of the silylating agent become chemically bonded to polymer molecules in the surface region of the substrate. (Notably, the term "silanization" is interchangeable with the term "silylation").

The silylation step according to the present invention may preferably be carried out as a vapor phase or liquid phase reaction, preferably using a silylating agent containing organosilicon groups and selected from the group comprising monofunctional and polyfunctional silylating agents that include amino groups.

Preferred monofunctional silylating agents include 3-(aminopropyl)triethoxysilane (APS), dimethylsilyldimethyl amine (DMSDMA), 1,1,3,3-tetramethyl disilazane (TMDS), N,N-dimethylamino trimethylsilane (TMSDMA), N,N-diethylaminotrimethylsilane (TMSDEA) and hexamethyldisilazane (HMDS). Preferred polyfunctional silylating agents include Bis(dimethylamino) methylsilane, Bis-(dimethylamino)dimethylsilane and 1,1,3,3,5,5-hexamethylcyclotrisilazane (HMCTS).

Gas phase silylation is preferably carried out in a vapor of silylating agent, most preferably in a nitrogen carrier gas at elevated temperatures, preferably in the range of about 140 to 200° C.

Notably, in the process of the present invention, liquid-phase silylation may also be used. The liquid phase silylation solution is comprised of two and possibly three components: 1) the silylating agent, 2) the transport solvent, and possibly, 3) a diffusion enhancer. The silylating agent is, as previously outlined, the chemical agent that carries the necessary silicon for binding to the activated polymeric surface. The transport solvent acts as the solvent for the silylating agent, and should be relatively inert otherwise. The diffusion enhancer is a solvent that dissolves the surface of the substrate slightly, allowing the silylating agent to diffuse deeper and more rapidly below the surface of the substrate, preferably throughout the entire surface region containing reactive hydrogen groups.

Preferred transport solvents are those that act as a solvent for the silylating agent, and are inert toward the substrate, that is, they do not dissolve or swell the substrate. The most preferred solvents are hydrocarbons, such as ethanol and aromatic solvents such as xylene, and aliphatic solvents such as n-decane.

Preferably, the silylating agent diffuses into the substrate to react with active hydrogen atoms throughout the activated surface region of the substrate. The diffusion rate of the silylating agent may preferably be increased by slight heating, up to about 60° C., and by the addition, to the silylation bath, of the diffusion enhancer. For polymers such as Kapton, PEEK and PET a diffusion enhancer such as n-methylpyrrolidone (NMP) can be added. Silylation is generally carried out at 50-80° C., the substrate being immersed in a solution of silylating agent for about 3 minutes to 24 hours.

After silylation, the polymeric surface is ready for deposition of metallic particles. The metal particles used in the present invention can be spheroid, ellipsoid, triangular or of any other geometry and preferably are deposited on the polymeric surface to form small islands. Metal particles, preferably noble metals, most preferably silver, may be chemically reduced on a surface.

The island particles may be prepared in clean beakers by reduction of metal ions using various reducing agents. [25]. For example, sodium hydroxide is added to a rapidly stirred silver nitrate solution forming a brown precipitate. Ammonium hydroxide is added to re-dissolve the precipitate. The solution is cooled and dried polymeric substrates are added to the beaker, followed by glucose. After stirring for 2 minutes, the mixture is warmed to 30° C. After 10-15 minutes, the mixture turns yellow-green and becomes cloudy. A thin film of silver particles has formed on the polymeric surfaces and then the polymeric substrate is rinsed with pure water prior to use.

Alternative procedures for preparing metal particles are also available [26-30]. Silver is primarily used because of the familiar color from the longer surface plasmon absorption of silver.

Determining the correct positioning of the fluorophore attached to a target molecule relative to the metallic particle is essential for maximum fluorescence enhancement geometries (distance dependence). The present inventors have previously conducted calculations for several probes. Similar calculations may also be done for many other commercially available fluorophores. By controlling the fluorophore environment, such as modifying the pH, the functional properties of the metallized polymeric surface/fluorophore sensor in terms of enhanced fluorescence and improved photostability may be determined. After each environmental change, spectroscopic data may be acquired, analyzed and assessed in terms of the probe functionality in various nano-sites. Such measurements will allow immediate comparison of the fluorophore and the relative distance that display substantial enhancement due to the appropriate proximity to the metal surface and those which are not affected (i.e. too far from metal surface) and can be used for fluorescence sensors on the nanometer scale.

Once the appropriate distance is determine between the fluorophore and metallic particle, the distance may be maintained by using Langmuir-Blodgett films with fatty acid spacers. The fatty acids may be from natural sources, including concentrated cuts or fractionations, or synthetic alkyl carboxylic acids. The Langmuir-Blodgett technique provides an accurate means of controlling film thickness and surface uniformity and allows an accurate control of the metal-fluorophore distance.

Further, metal-fluorophore distances may be achieved by using polymer films. Examples of the polymer include, but not limited to, polyvinyl alcohol (PVA). Absorbance measurements and ellipsometry may be used to determine polymer film thickness. One type of polymer films may include spin coated polymer films.

The film spacer layer may be one or multiple layers formed from an oxide. The oxide layer may be formed from a deposition technique, such as vapor deposition. Preferably, the oxide is a silicon oxide, more preferably, $SiO_2$. The vapor deposition of $SiO_2$ is a well established technique for the controlled deposition of a variety of substrates.

Further, proteins or oligonucleotides may be bound to silver surfaces or particles by using amino or sulfhydryl groups using methods known in the art. The length of the complimentary captured protein or oligonucleotide, within the enhancement region (40-500 Å), can also be determined by the metal enhanced fluorescence experiments with the Langmuir-Blodgett films and spin coated PVA, as discussed above. Fluorophore-metal distances that provide maximum fluorescence enhancement are determined empirically and are thus used in determining the amino acid or DNA sequence length to use for capturing the sequences so that fluorescence of same is optimally enhanced.

Detection devices applicable for detecting fluorescence emissions include, but not limited to visual inspection, digital (CCD) cameras, video cameras, photographic film, or the use of current instrumentation such as laser scanning devices, fluorometers, luminometers, photodiodes, quantum counters, plate readers, epifluorescence microscopes, scanning microscopes, confocal microscopes, capillary electrophoresis detectors, or other light detector capable of detecting the presence, location, intensity, excitation and emission spectra, fluorescence polarization, fluorescence lifetime, and other physical properties of the fluorescent signal.

The following examples illustrate the present invention and are not intended to limit the same.

EXAMPLES

A polycarbonate film (PC) was modified using chemical modification for silver deposition and therefore metal-enhanced fluorescence. Base catalyzed hydrolysis of the PC film readily created additional surface functionality for silver island film deposition. Polycarbonate was chosen as the polymer of interest due to its widespread use in biotechnology [6, 12, 13].

Metal-enhanced fluorescence is known to be a through space phenomenon, where the close proximity of fluorophores to silver nanostructures results in quenching of the emission [1, 2, 5]. The fluorophore was positioned about 4 nm from the metallic surface using a labeled protein, namely FITC-HSA. The disclosed results clearly show that plastics can indeed be modified for silver deposition and notable enhancements in fluorescence emission can be achieved from the plastic substrates, similar to that observed from glass [5].

Materials and Methods

Polycarbonate (PC) films with ≈50 pm thickness were cut into 75×25 mm pieces and placed onto Fisher brand glass microscope slides in order to provide support for the films. PC films were hydrolyzed in 2 M aqueous NaOH solution for 1 minute and rinsed with deionized water. PC films were then transferred onto new glass slides and finally dried under a stream of cooled air. The hydrolyzed PC films were silanized with a 2% v/v solution of 3-(aminopropyl)triethoxysilane (APS) in denatured ethanol for 2 hours. The APS coated PC films were removed from the solution and rinsed several times with ethanol and deionized water to remove the unbound APS. Silver Island Films (SiFs) were formed on half of the silanized PC films (the non-silvered half is used as a control) similar to our previous procedure[3,5]. SiFs were also formed on virgin PC films, i.e. unmodified films.

In previous reports of metal-enhanced fluorescence (MEF), silvered glass or quartz surfaces were coated with fluorophore labeled protein [5]. This same experimental format has been adopted for two main reasons, the first, being that the protein coverage with Human Serum Albumin (HSA) is known to bind to silvered surfaces and indeed forms a monolayer [4,5] and secondly, the dimensions of the protein being such that the protein allows for a mean ≈4 nm separation of the silver and the fluorophore, MEF being a through space phenomenon [1,2,5].

Binding the FITC-HSA to the PC films was accomplished by soaking in a 10 uM FITC-HSA solution for 2 hours, followed by rinsing with water to remove the unbound material. PC films were then transferred onto new glass slides. Both the unsilvered and silvered PC films were coated with labeled HSA, which is known to passively absorb to noble metal surfaces and form a ≈4 nm thick protein monolayer, allowing us to study the fluorescence spectral properties of noncovalent FITC-HSA complexes in the absence and presence of SiFs. By equally coating a PC film with FITC-HSA determination of the enhancement factor (benefit) obtained from using the silver, i.e. Intensity on Silver/Intensity on PC film, given that both surfaces are known to have an ≈ equal monolayer coverage [5].

All absorption measurements were performed using a HP 8453 UV-Vis spectrophotometer. Fluorescence measurements on PC films were performed by placing the films on a stationary stage equipped with a fiber-optic mount on a 15 cm-long arm (normal to sample). The output of the fiber was connected to an Ocean Optics HD2000 spectrofluorometer to measure the fluorophore emission spectra. The excitation was from the second harmonic (470 nm) of the diode-pumped Nd:YV04 laser (compact laser pointer design, output power ≈30 mW) at angle of 45 degrees. The emission was observed through a 500 nm long-pass filter (Edmund Scientific).

The real-co/or photographs of FITC-HSA on non-silvered PC films and PC films with SiFs, were taken with a Olympus Digital camera (C-740, 3.2 Mega Pixel, 10× Optical Zoom) using the same long-pass filter that was used for the emission spectra. Time-resolved intensity decays were measured using reverse start-stop time-correlated single-photon counting (TCSPC) [14] with a Becker and Hickl Gmbh 630 SPC PC card and an un-amplified MCP-PMT. Vertically polarized excitation at 440 nm was obtained using a pulsed laser diode, 1 MHz repetition rate. The intensity decays were analyzed in terms of the multi-exponential model:

$$I(t) = \sum_i \alpha_i \exp(-t/\tau_i)$$

where $\alpha_i$ are the amplitudes and $\tau_i$ are the decay times, $\Sigma \alpha_i = 1.0$. The fractional contribution of each component to the steady-state intensity is given by:

$$f_i = \frac{\alpha_i \tau_i}{\sum_i \alpha_i \tau_i}$$

The mean lifetime of the excited state is given by:

$$\bar{\tau} = \sum_i f_i \tau_i$$

The values of $\alpha_i$ and $\tau_i$ were determined by non-linear least squares impulse reconvolution with a goodness-of-fit $\chi^2_R$ criterion. [14]

Figure 2:
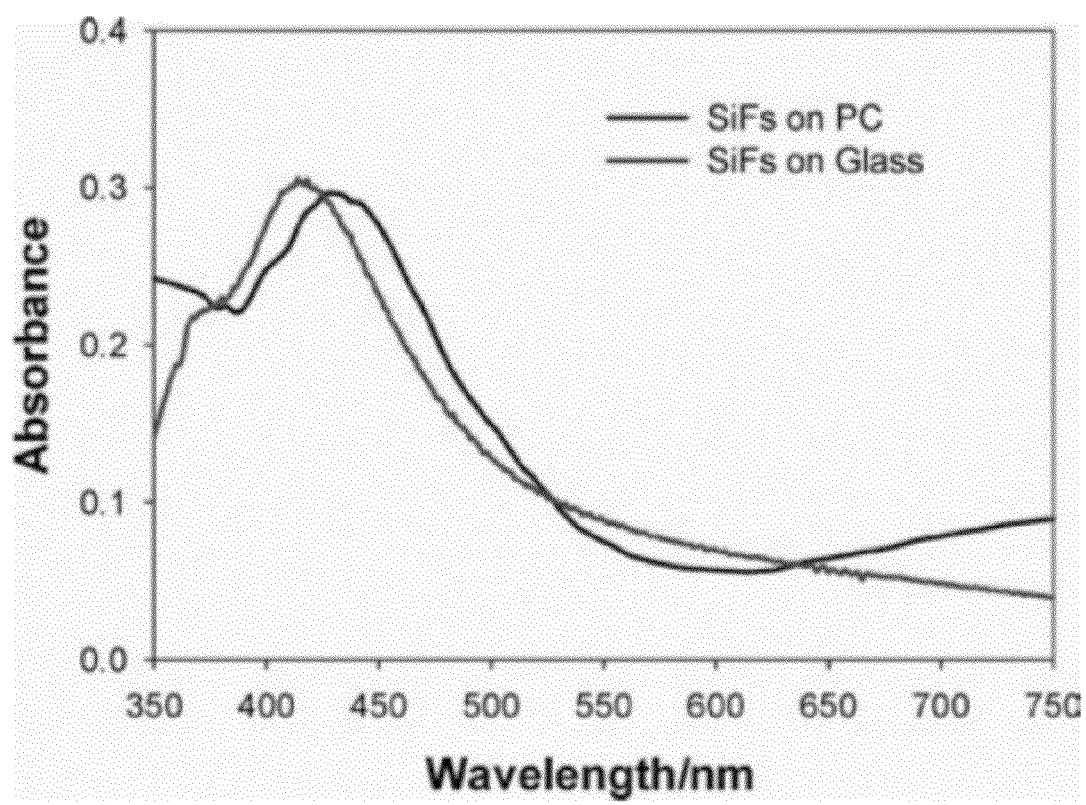
FIG. 2 shows absorption spectra of Silver Island Films, SiFs, grown on both modified PC and glass.

Initial attempts at directly depositing silver island films (SiFs) onto plastic substrates resulted in relatively poor silver attachment to the virgin polycarbonate (PC) surface, FIG. 1—Left. However, after etching the PC film in 2 M NaOH for 1 min, followed by silanization providing an amino coating on the surface using APS, 3-(aminopropyl)triethoxysilane, silver island films were readily formed, FIG. 1—right, and could not be washed from the surface. It is theorized that the strong base provided additional surface hydroxyl groups for APS attachment by hydrolyzing the PC film, a procedure previously reported by Dauginet, et al [12]. For the thin films used in this report, immersion in 2 M hydroxide for 1 minute was found to be sufficient for SiF preparation on the plastic surface, where the SiFs have a maximum optical density around 0.3, consistent with previous reports [3,5]. The plasmon absorption band for the SiFs was also found to be slightly red-shifted on the PC film as compared to that typically observed on glass substrates as shown in FIG. 2 [3,5].

To test the silver coated plastic surfaces for metal-enhanced fluorescence, unmodified and modified films were equally coated with fluorescein labeled HSA (Human Serum Albumin), as shown in FIG. 3, where the FITC-HSA has been shown to be an ideal labeled protein [3,4,5], with regard to positioning the fluorophore a couple of nanometers from the silver nanoparticles to facilitate metal-enhanced fluorescence [1,2].

FIG. 3 shows that the emission of fluorescein is substantially greater on the silver island film coated modified PC films as compared to an equal coating on PC, but without any SiFs. In addition, no emission could be observed from the FITC-HSA coated virgin PC, demonstrating the need to modify the surface for metal-enhanced fluorescence. Interestingly, even without silver, etching the plastic with hydroxide provided for a greater protein coverage than the virgin PC film, FIG. 3. The transmission of the cut-off filter used is also shown in FIG. 3 and accounts for the sharp rising edge of the emission spectra.

The metal-enhanced fluorescence from the silver coated modified plastic film was found to be approximately 7 times greater than the modified PC film but with no SiFs (i.e. the control sample). This relatively large increase in emission intensity could also be seen visually, FIG. 4, through the same long pass filter as used in FIG. 3. As the 470 nm laser excitation is moved from the unsilvered plastic (Middle) to the silvered plastic side, (Bottom), a dramatic increase in fluorescein emission was seen.

Figure 5:
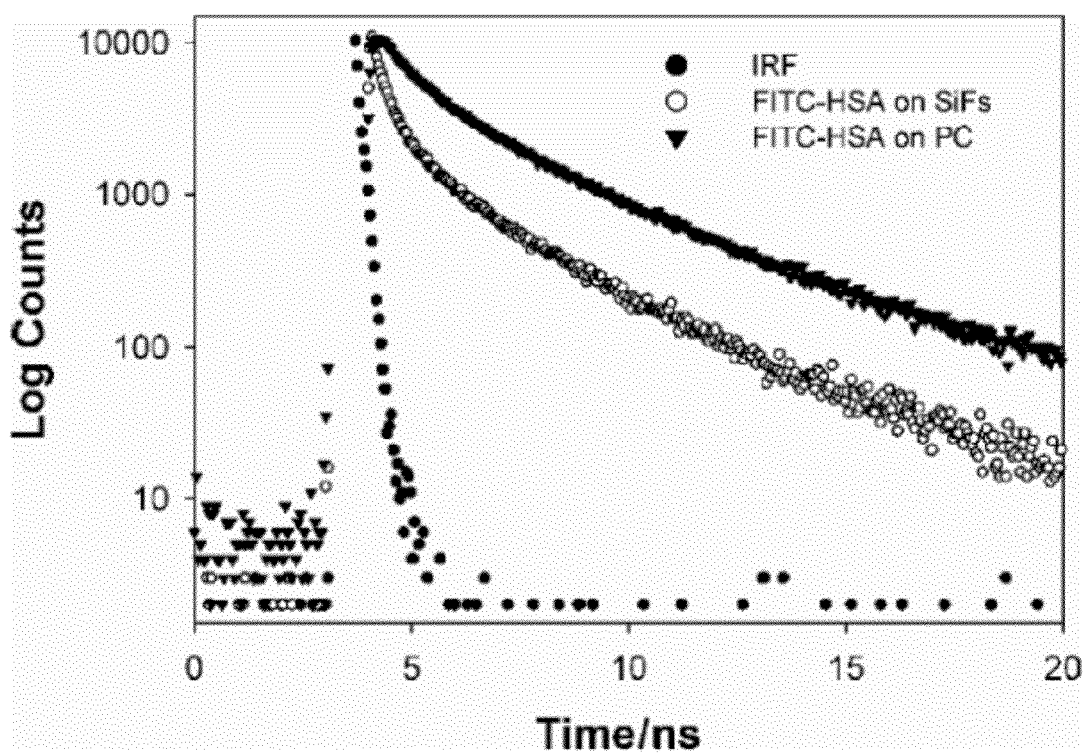
FIG. 5 shows the intensity decays of FITC-HSA on silvered and unsilvered modified PC: The instrumental response Function, IRF, is also shown.

Metal-enhanced intensity, accompanied fluorescence resulted in both increased emission intensity, accompanied by a reduction in fluorophore lifetime, i.e. a radiative modification [1-5]. FIG. 5 shows the reduction in lifetime on the SiFs as

TABLE I

Analysis of the Intensity Decay of FITC-HSA on Silvered and Unsilvered Modified PC, Measured Using the Reverse Start-Stop Time-Correlated Single Photon Counting Technique and the Multi-Exponential Model

| Sample | $\alpha_1$ | $\tau_1$ (ns) | $\alpha_2$ | $\tau_2$ (ns) | $\alpha_3$ | $\tau_3$ (ns) | $\bar{\tau}$ (ns) | $\langle\tau\rangle$ (ns) | $\chi_R^2$ |
|---|---|---|---|---|---|---|---|---|---|
| FITC-HSA on SiFs | 0.290 | 0.090 | 0.330 | 0.946 | 0.380 | 3.54 | 3.00 | 1.68 | 1.14 |
| FITC-HSA on PC | 0.079 | 0.289 | 0.289 | 1.182 | 0.632 | 3.50 | 3.16 | 2.58 | 0.89 | plastic. The amplitude weighted lifetime was found to decrease from 2.58 ns on the unsilvered plastic to 1.68 ns on the silvered plastic, FIG. 5 and Table I.

Figure 6:
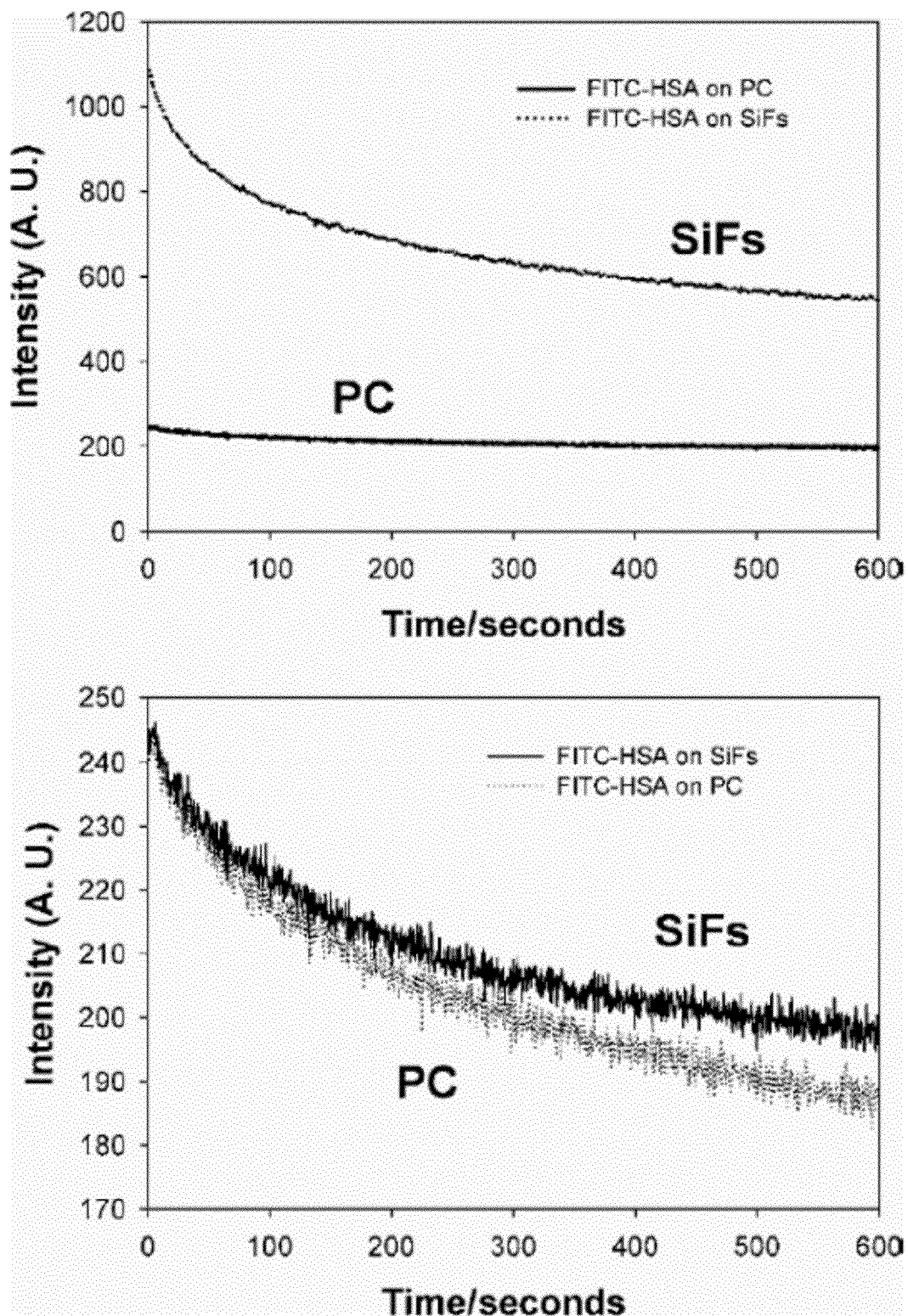
FIG. 6 shows emission intensity Vs time of FITC-HSA on both silvered and unsilvered modified PC with constant 470 nm excitation, Top; and with the laser power adjusted to give the same initial steady state fluorescence intensity, Bottom.

The photostability of the FITC-HSA was measured on both the unsilvered and silvered modified PC film, FIG. 6. Using the same laser power significantly more fluorescence was observed from the silvered plastic, by simply considering the integrated area under the respective curves, FIG. 6-Top. However, when the laser power on the silver surface was attenuated to give the same initial emission intensity as observed on the unsilvered but modified plastic, similar photostability characteristics, FIG. 6—bottom were noticed.

By base hydrolysis of thin polycarbonate films more surface functionality for silver deposition was provided. Subsequently, by coating these silvered surfaces with a labeled protein, metal-enhanced fluorescence was observed in an approximate 7-fold increase in fluorescein emission intensity observed from modified and silvered plastic as compared to a modified but unsilvered PC film. Further, by comparing the emission intensity from the virgin PC film to the modified and silvered film, a substantial increase in fluorophore emission intensity can be realized. Given the widespread use of plastic substrates in fluorescence based clinical assays and in drug discovery (e.g. HTS well plates), then simple surface modifications of plastics could facilitate silver depositions for metal-enhanced fluorescence. Alternatively, unmodified hydrophilic plastics with an abundance of surface hydroxyl or even amino groups [15] could be ideal for silver deposition and alleviate the need for surface plastic modification. In addition, surface plastic modification using specific light wavelengths to break covalent bonds and therefore provide for additional polymer surface functionality will be applicable to modification according to the present invention. This reagentless approach could readily be used to prepare plastics for silver deposition.

References

The contents of all references cited herein are hereby incorporated by reference herein for all purposes.

1. C. D. Geddes and J. R. Lakowicz (2002) Metal-enhanced fluorescence, J.Fluoresc. 12(2), 121-129.

2. J. R. Lakowicz (2001) Radiative decay engineering: Biophysical and biomedical applications, Appl. Biochem. 298, 1-24.

3. J. R. Lakowicz, Y. Shen, S. D'Auria, J. Malicka, J. Fang, Z. Grcyzynski and I. Gryczynski (2002) Radiative decay engineering 2. Effects of silver island films on fluorescence intensity, lifetimes, and resonance energy transfer, Anal.Biochem. 301, 261-277.

4. C. D. Geddes, H. Cao, I. Gryczynski, Z. Gryczynski, J. Fang, and J. R. Lakowicz (2003) Metal-enhanced fluorescence due to silver colloids on a planar surface: potential applications of lndocyanine green to in vivo imaging. J Phys Chem A 107, 3443-3449.

5. C. D. Geddes, K. Aslan, I. Gryczynski, J. Malicka, and J. R. Lakowicz (2004) Noble Metal Nanostructure for Metal-Enhanced Fluorescence, Reviews in Fluorescence 2004, Ed. C. D. Geddes, pp. 365401, Springer, New York.

6. Y. Liu, D. Ganser, A. Schneider, P. Grodzinski, N. Kroutchinina (2001) Microfabricated Polycarbonate CE Devices for DNA Analysis, Anal Chem 73, 4196-4201.

7. M. Boerner, M. Kohl, F. Pantenburg, W. Bather, H. Hein, W. Schomburg, (1996) Microsyst Technol, 2, 149-1 52.

8. M. A. Roberts, J. S. Rossier, P. Bercier, H. Girault, H. (1997) UV Laser Machined Polymer Substrates for the Development of Microdiagnostic Systems, Anal Chem, 69, 2035-2042.

9. L. Martynova, L. E. Locascio, M. Gaitan, G. W. Kramer, R. G. Christensen, W. MacCrehan (1997) Fabrication of plastic microfluid channels by imprinting methods, Anal Chem, 69,4783-4789.

10. J. Xu, L. Locascio, M. Gaitan, C. S. Lee, (2000) Room-Temperature Imprinting Method for Plastic Microchannel Fabrication, Anal Chem, 72, 1930- 1933.

11. R.M. McCormick, R. J. Nelson, M. G. Alonso-Amigo, D. J. Benvegnu, H. H. Hooper (1997) Microchannel Electrophoretic Separations of DNA in Injection-Molded Plastic Substrates, Anal Chem, 69, 2626-2630.

12. L. Dauginet, A. S. Duwez, R. Legras, S. Demoustier-Champagne, Surface Modification of Polycarbonate and Poly (ethyleneterephthalate) Films and Membranes by Polyelectrolyte Deposition, Langmuir, 17, 3952-3957.

13. Y. Xu, B. Vaidya, A. B. Patel, S. M. Ford, R. L. McCarley, S. A. Soper (2003) Solid-Phase Reversible Immobilization in Microfluidic Chips for the Purification of Dye-Labeled DNA Sequencing Fragments, Anal Chem, 75, 2975 -2984.

14. J. R. Lakowicz (1999) Principles of Fluorescence Spectroscopy; Kluwer: New York.

15. W. Ward, T. J. McCarthy, (1989) In Encyclopedia of Polymer Science and Engineering, 2nd ed.; Mark, H. F., Bikales, N. M., Overberger, C. G., Menges, G., Kroschwitz, J. I., Eds.; John Wiley and Sons: New York, 1989; suppl. vol. pp. 674-689.

16. D M. Coates, S. L Kaplan,.; (1996) Modification of Polymeric Material Surfaces with Plasmas, Chapter IV of Plasma Processing of Advanced Materials, edited by George A. Collins and Donald J. Rej, MRS Bulletin.

17. A. Wokaun, H. P. Lutz, A. P. King, U. P. Wild and R. R. Ernst (1983). Energy transfer in surface enhanced fluorescence, J. Chem. Phys., 79(1), 509-514.

18. W. R. Holland and D. G. Hall (1985). Waveguide mode enhancement of molecular fluorescence. Optics Letts., 10(8), 414-416.

19. A. M. Glass, P. F. Liao, J. G. Bergman and D. H. Olson (1980). Interaction of metal particles with adsorbed dye molecules: absorption and luminescence. Optics Letts., 5(9), 368-370.

20. W. L. Barnes (1998). Fluorescence near interfaces: The role of photonic mode density, J. Modem Optics, 45(4), 661-699.

21. J. R. Lakowicz, Y. Shen, S. D'Auria, J. Malicka, J. Fang, Z. Gryczynski and I. Gryczynski (2002). Radiative Decay Engineering 2. Effects of silver island films on fluorescence intensity Lifetimes and Resonance energy transfer, Anal. Biochem., 301, 261-277.

22. I. Gryczynski, J. Malicka, L. Gryczynski, C. D. Geddes and J. R. Lakowicz (2002) The CFS engineers the intrinsic radiative decay rate of low quantum yield fluorophores, J. FJuoescence, 12(1), 11-13.

23. J. R. Lakowicz, I. Gryczynski, Y. B. Shen, J. Malicka, and Z. Gryczynski, (2001). Intensified fluorescence, Photonics Spectra, 35(10), 96-104.

24. C. D. Geddes and J. R. Lakowicz (2002). Metal-Enhanced Fluorescence, J. Flourescence, 12(2), 121-129.

25. L. Rivas, S. Sanchez-Cortes, J. V. Garcia-Ramos and G. Morcillo, Growth of Silver Colloidal Particles Obtained by Citrate Reduction to Increase the Ramen Enhancement Factor, Langmuir, 17(3), 574-577 (2001).

26. N. Shirtcliffe, U. Nickeland S. Schneider, Reproducible preparation of silver sols with small particle size using borohydride reduction: For use as nuclei for preparation of large particles, J. Colloid Interface Sci., 211(1), 122-129 (1999).

27. I. Pastoriza-Santos, and L. M. Liz-Marzan, Reduction of silver nanoparticles in DMF. Formation of monolayers and stable colloids, Pure Appl. Chem., 72(1-2), 83-90 (2000).

28. I. Pastoriza-Santos, C. Serra-Rodriquez and L. M. Liz-Marzan, Self-assembly of silver particle monolayers on glass from Ag$^+$solutions in DMF, J. Colloid Interface Sci., 221(2), 236-241 (2000);

29. R. Bright, M. D. Musick and M. J. Natan, Preparation and characterization of Ag colloid monolayers, Langmuir, 14(20), 5695-5701 (1998).

30. F. Ni and T. M. Cotton, Chemical procedure for preparing surface-enhanced Raman scattering active silver films, Anal. Chem., 58(14), 3159-5163 (1986).

That which is claimed is:

1. A fluorescence sensing device comprising:
   a modified polymeric surface comprising amino-terminated functional groups;
   nanometer sized metallic particles positioned on the modified polymeric surface, wherein the metallic particles can be any geometric shape; and
   a fluorophore compound communicatively linked, via a spacer, to the metal particles at a sufficient distance to enhance the fluorescence of the fluorophore when exposed to electromagnetic radiation from an electromagnetic source.

2. The fluorescence sensing device according to claim 1, further comprises a detection device for detecting fluorescence emissions.

3. The fluorescence sensing device according to claim 1, wherein the polymeric surface is polycarbonate.

4. The fluorescence sensing device according to claim 1, wherein the electromagnetic energy is in the ultraviolet range.

5. The fluorescence sensing device according to claim 1, wherein the polymeric surface is fabricated of polyamide, polycarbonate, polyester, polyetherimide, polyimide, polynitrocellulose, polyethylene, polypropylene, poly(ethylenevinylacetate), poly-2-pentene, polyphenylene oxide, polyphenylene sulfide, polysulfone, and polystyrene.

6. The fluorescence sensing device according to claim 1, wherein the spacer is an amino acid or nucleotide sequence.

7. The fluorescence sensing device according to claim 1, wherein the modified polymeric surface has been modified with a chemical or physical etching agent thereby providing an increased number of exposed hydroxyl groups or amine group on the polymeric surface relative to an unmodified polymeric surface and wherein modified polymeric material is coated with an amine containing silane to provide an amino-terminated polymeric material for binding with deposited noble metals.

8. The fluorescence sensing device according to claim 7, wherein the amine-containing silane is selected from the group consisting of 3-(aminopropyl)triethoxysilane (APS), dimethylsilyldimethyl amine (DMSDMA), 1,1,3,3-tetramethyl disilazane (TMDS), N,N-dimethylamino trimethylsilane (TMSDMA), N,N-diethylaminotrimethylsilane (TMSDEA), hexamethyldisilazane (HMDS), Bis(dimethylamino) methylsilane, Bis-(dimethylamino)dimethylsilane and 1,1,3,3,5,5-hexamethylcyclotrisilazane (HMCTS).

9. The fluorescence sensing device according to claim 7, wherein the amine-containing silane is 3-(aminopropyl)triethoxysilane (APS).

10. The fluorescence sensing device according to claim 7, wherein the chemical etching agent is selected from the group consisting of NaOH, $NH_4OH$, LiOH, KOH or $N(CH_3)_4OH$.

11. The fluorescence sensing device according to claim 7, wherein the chemical etching agent is NaOH and the etching is conducted at a temperature ranging from about 15° C. to about 45° C. for a time ranging from about 1 minute to about 1 hour.

12. The fluorescence sensing device according to claim 7, wherein the physical etching agent is a dose of UV radiation, in the presence of oxygen.

13. The fluorescence sensing device according to claim 1, wherein the device is in the form of a kit comprising
   a container comprising a layer of immobilized metal particles deposited on a modified polymeric substrate, wherein an immobilized probe is connected to the metal particles and wherein the immobilized probe has an affinity for the target molecule; and
   a fluorophore having an affinity for the target molecule, wherein the binding of the target molecule to both the immobilized probe and fluorophore causes the fluorophore to be positioned a sufficient distance from the immobilized metal particles to enhance fluorescence emission.

* * * * *